(12) United States Patent
Okada

(10) Patent No.: US 8,912,363 B2
(45) Date of Patent: Dec. 16, 2014

(54) CHLORINATED POLYETHER AND POLYURETHANE OBTAINED THEREFROM

(75) Inventors: Takashi Okada, Mie (JP); Megumi Okada, legal representative, Aichi (JP); Mayuko Okada, legal representative, Aichi (JP); Yuko Okada, legal representative, Aichi (JP)

(73) Assignee: Tosoh Corporation, Shunan-Shi (JP)

( * ) Notice: Subject to any disclaimer, the term of this patent is extended or adjusted under 35 U.S.C. 154(b) by 0 days.

(21) Appl. No.: 12/995,634

(22) PCT Filed: Jun. 9, 2009

(86) PCT No.: PCT/JP2009/060545
§ 371 (c)(1),
(2), (4) Date: Dec. 1, 2010

(87) PCT Pub. No.: WO2009/151055
PCT Pub. Date: Dec. 17, 2009

(65) Prior Publication Data
US 2011/0124761 A1    May 26, 2011

(30) Foreign Application Priority Data
Jun. 10, 2008  (JP) ................. 2008-151472

(51) Int. Cl.
| C08G 18/00 | (2006.01) |
| C07C 43/00 | (2006.01) |
| C08G 18/32 | (2006.01) |
| C08G 65/22 | (2006.01) |
| C08G 18/66 | (2006.01) |
| C07C 43/11 | (2006.01) |
| C08G 18/50 | (2006.01) |
| C08G 101/00 | (2006.01) |

(52) U.S. Cl.
CPC .... *C08G 18/5009* (2013.01); *C08G 2101/0083* (2013.01); *C08G 18/3206* (2013.01); *C08G 65/223* (2013.01); *C08G 2101/00* (2013.01); *C08G 18/6674* (2013.01); *C07C 43/11* (2013.01)
USPC ............... 568/614; 521/174; 528/44; 528/76; 528/77

(58) Field of Classification Search
USPC .......... 521/174; 528/44, 76, 77; 568/614, 174
See application file for complete search history.

(56) References Cited

U.S. PATENT DOCUMENTS

| 3,260,687 | A | * | 7/1966 | Postol ........................ 521/123 |
| 3,409,593 | A |   | 11/1968 | Messwarb et al. |
| 3,419,532 | A | * | 12/1968 | Jackson ........................ 528/77 |
| 3,928,501 | A |   | 12/1975 | Vandenberg |
| 4,144,395 | A | * | 3/1979 | Murphy et al. ............. 560/200 |
| 4,149,987 | A | * | 4/1979 | Austin et al. ................. 568/610 |
| 4,184,024 | A | * | 1/1980 | Klein ........................... 521/167 |
| 4,228,310 | A | * | 10/1980 | Speranza et al. ............. 568/620 |
| 4,318,838 | A | * | 3/1982 | Gallagher et al. ............ 524/444 |
| 4,359,549 | A | * | 11/1982 | Gallagher et al. ............ 524/791 |
| 4,539,395 | A |   | 9/1985 | Shimizu et al. |
| 4,555,531 | A | * | 11/1985 | Christman .................... 521/167 |
| 4,585,807 | A | * | 4/1986 | Christman .................... 521/167 |
| 4,588,803 | A | * | 5/1986 | Christman ...................... 528/78 |
| 4,605,725 | A | * | 8/1986 | Christman ...................... 528/77 |
| 4,943,626 | A |   | 7/1990 | McGrath et al. |
| 5,095,061 | A |   | 3/1992 | Chavez, Jr. et al. |
| 5,103,028 | A |   | 4/1992 | Falling et al. |
| 5,264,595 | A | * | 11/1993 | Falling et al. ................. 549/540 |
| 5,313,000 | A |   | 5/1994 | Stewart |

(Continued)

FOREIGN PATENT DOCUMENTS

| CN | 1039816 A | 2/1990 |
| EP | 0352819 A2 | 1/1990 |

(Continued)

OTHER PUBLICATIONS

Chinese Office Action with the English translation dated Mar. 12, 2012, for Application No. 200980121953.0.

(Continued)

*Primary Examiner* — Melissa Rioja
(74) *Attorney, Agent, or Firm* — Birch, Stewart, Kolasch & Birch, LLP

(57) ABSTRACT

Provided is a chlorinated polyether which has excellent solubility in solvents and excellent thermal stability, has the excellent effect of improving the adhesion of coating materials, inks, and adhesives to polyolefins, can be expected to be usable as a flame retardant, and is useful also as a novel starting material for polyurethanes. The polyether is a novel chlorinated polyether containing, as a repeating unit, at least one of the chlorinated-ether residue represented by the following formula (1) and the chlorinated-ether residue represented by the following formula (2). Also provided is a novel polyurethane obtained therefrom.

[Chem. 1]

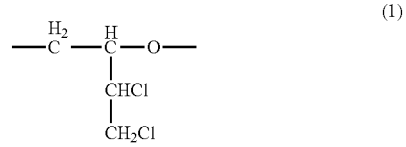

[Chem. 2]

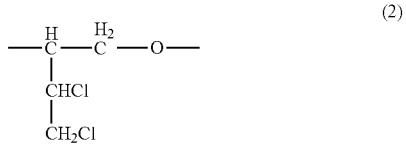

3 Claims, No Drawings

(56) References Cited

U.S. PATENT DOCUMENTS

| | | | | |
|---|---|---|---|---|
| 5,342,541 | A | * | 8/1994 | Chavez, Jr. et al. ...... 252/182.27 |
| 5,468,839 | A | * | 11/1995 | Suppes et al. ................. 528/403 |
| 5,478,867 | A | * | 12/1995 | Tabor ............................ 521/163 |
| 5,705,547 | A | * | 1/1998 | Richards et al. ............. 524/111 |
| 6,451,926 | B1 | | 9/2002 | Kuo et al. |
| 2005/0267287 | A1 | | 12/2005 | Adkins |

FOREIGN PATENT DOCUMENTS

| | | |
|---|---|---|
| EP | 0466150 A1 | 1/1992 |
| JP | 58-176207 A | 10/1983 |
| JP | 59-196361 A | 11/1984 |
| JP | 2-196827 A | 8/1990 |
| JP | 2005-336491 A | 8/1990 |
| JP | 4-226528 A | 8/1992 |
| JP | 4-505934 A | 10/1992 |
| JP | 6-510301 A | 11/1994 |
| JP | 2001-230066 A | 8/2001 |
| JP | 2002-543256 A | 12/2002 |
| WO | WO 00/66649 A1 | 11/2000 |

OTHER PUBLICATIONS

International Search Report for PCT/JP2009/060545, mailed on Jul. 14, 2009.

Saishin Poriuretan No Sekkei/Kaishitsu To K•kin•ka Gijutsu Zensh• , pp. 305-319, published by Technical Information Institute Co., Ltd. (2007).

Sangermano et al., "The Photoinitiated Cationic Polymerization of 3,4-Epoxy-1-butene", American Chemical Society, 2003, Chapter 23, No. 847, pp. 266-276, U.S.A.

Chinese Office Action for Chinese Application No. 200980121953.0 dated Sep. 13, 2012 with partial English translation.

Extended European Search Report for European Application No. 09762485.2 dated Oct. 12, 2012.

Chinese Office Action, dated Jun. 7, 2013, for Chinese Application No. 200980121953.0 with a full English translation.

Chinese Office Action dated Jan. 7, 2013, for Chinese Application No. 200980121953.0 with English Translation.

Japanese Office Action dated Feb. 4, 2014 and its English Translation for Japanese Patent Application No. 2009-137294.

* cited by examiner

CHLORINATED POLYETHER AND POLYURETHANE OBTAINED THEREFROM

TECHNICAL FIELD

The present invention relates to a novel chlorinated polyether for use as a starting material for resins such as polyurethanes and polyesters and as a surfactant, lubricant, or the like, and to a novel polyurethane obtained from the chlorinated polyether.

BACKGROUND ART

Polyol compounds are extensively used in applications such as starting materials for resins, e.g., polyurethanes and polyesters, surfactants, and lubricants.

In recent years, polyurethane foam is in use as heat insulators and cushioning materials in a wide variety of fields including building materials, electrical appliances, furniture, and motor vehicles because the foam has satisfactory heat-insulating properties and cushioning properties. Although the polyurethane foam has hitherto been produced through blowing with a chlorofluorocarbon gas, shifting from chlorofluorocarbon-based blowing agents to chlorofluorocarbon-free blowing materials, e.g., carbon dioxide, is proceeding due to the recent environmental problems. Polyurethane foam produced through blowing with carbon dioxide has been proposed, for which the carbon dioxide generated by subjecting water to reaction with an isocyanate is used as a blowing agent as one of such chlorofluorocarbon-free blowing materials (see, for example, patent document 1).

Polyurethanes, which are formed from organic compounds, further have a problem that they are flammable. It is hence required to impart high flame retardancy thereto, and use of many flame retardants has been proposed (see, for example, non-patent document 1).

In the case where polyurethanes are used as raw materials in fields such as urethane coating materials and inks, the polyurethanes are required to have improved coating property to polyolefins. A technique in which a chlorinated polypropylene is used as a binder has been proposed (see, for example, patent document 2). However, the chlorinated polypropylene used in that technique, although soluble in aromatic solvents, are insoluble in other solvents and have been used only in applications where use of aromatic solvents is permitted. As a technique for overcoming this problem, use of a chlorinated polypropylene glycol has been proposed (see, for example, patent document 3).

However, the technique proposed in patent document 1 has a problem that since carbon dioxide has a smaller molecular size than chlorofluorocarbons, the carbon dioxide is apt to come out of the polyurethane foam and the heat-insulating performance and dimensional accuracy of the foam decrease with the lapse of time. Especially in slab products cut out of the polyurethane foam (block) produced through blowing with carbon dioxide, which is easy to handle, the carbon dioxide present within the foam is apt to come out because of the absence of a skin layer on the surface thereof. It has hence been difficult to use such slab products for heat insulation.

The technique in which a flame retardant is added in order to impart flame retardancy, as proposed in non-patent document 1, has had a problem that since the flame retardant generally is a low-molecular compound, the flame retardant migrates to the surface of the polyurethane with the lapse of time, resulting in stickiness, etc.

Furthermore, the chlorinated polypropylene glycol proposed in patent document 3 has a problem that the chlorinated polypropylene glycol is poor in thermal stability and storage stability to cause dehydrochlorination with the lapse of time, although superior in that the chlorinated polymer has improved solubility in solvents and satisfactory adhesion to polyolefins.

PRIOR-ART DOCUMENTS

Patent Documents

Patent Document 1: JP-A-2001-230066
Patent Document 2: JP-A-58-176207
Patent Document 3: JP-A-59-196361

Non-Patent Document

Non-Patent Document 1: *Saishin Poriuretan No Sekkei/Kaishitsu To Kōkinōka Gijutsu Zenshū*, p. 305, published by Technical Information Institute Co., Ltd.

SUMMARY OF THE INVENTION

Problems that the Invention is to Solve

An object of the invention, which has been achieved in view of the background techniques described above, is to provide a novel chlorinated polyether as a useful material which is effective in inhibiting the carbon dioxide or the like from coming out of polyurethane foam produced through blowing with a blowing agent such as carbon dioxide, can be used also as a flame retardant, has excellent solubility in solvents and excellent thermal stability, and gives a polyurethane that has improved adhesion to polyolefins when used as a coating material, ink, or adhesive. Another object is to provide a novel polyurethane obtained from the chlorinated polyether.

Means for Solving the Problems

The present inventor diligently made investigations in order to overcome the problems described above. As a result, he has found out a novel chlorinated polyether which has excellent solubility in solvents and excellent thermal stability and gives a polyurethane that is excellent also in gas barrier properties, adhesiveness, and flame retardancy. The invention has been thus completed.

Namely, the invention relates to the chlorinated polyether shown below and a polyurethane obtained therefrom.

[1] A chlorinated polyether containing, as a repeating unit, at least one of the chlorinated-ether residue represented by the following formula (1) and the chlorinated-ether residue represented by the following formula (2).

[Chem. 1]

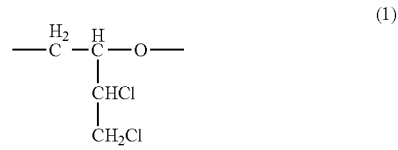

(1)

[Chem. 2]

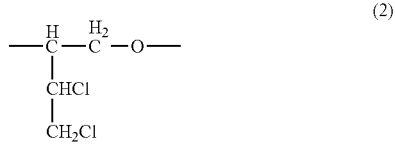

[2] The chlorinated polyether according to [1] above which has a hydroxyl value of 1-1,000 (mg-KOH/g).

[3] The chlorinated polyether according to [1] or [2] above which has a number-average molecular weight of 200-10,000.

[4] A process for producing the chlorinated polyether according to any one of [1] to [3] above, the process comprising conducting ring-opening polymerization of the chlorinated epoxy compound represented by the following formula (3) in the presence of an acid catalyst using an active-hydrogen-containing compound as a polymerization initiator.

[Chem. 3]

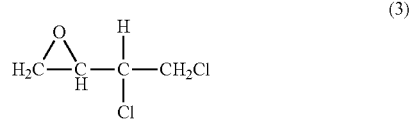

[5] A polyurethane comprising a product of the reaction of the chlorinated polyether according to any one of [1] to [3] above with a polyisocyanate compound.

[6] A process for producing a polyurethane, the process comprising subjecting the chlorinated polyether according to any one of [1] to [3] above to reaction with a polyisocyanate compound.

Advantages of the Invention

The chlorinated polyether of the invention has excellent solubility in solvents and excellent thermal stability, gives a polyurethane having the excellent effect of improving the adhesion of coating materials, inks, and adhesives to polyolefins, and can be expected to be usable as a flame retardant. In addition, the chlorinated polyether is useful also as a novel starting material for polyurethanes.

MODES FOR CARRYING OUT THE INVENTION

The invention will be explained below in detail.

The chlorinated polyether of the invention is a novel chlorinated polyether containing, as a repeating unit, at least one of the chlorinated-ether residue represented by the above-described formula (1) and the chlorinated-ether residue represented by the above-described formula (2).

Examples thereof include: a polymer containing the chlorinated-ether residue represented by the formula (1) as a repeating unit; a polymer containing the chlorinated-ether residue represented by the formula (2) as a repeating unit; and a polymer containing the chlorinated-ether residue represented by the formula (1) and the chlorinated-ether residue represented by the formula (2) as repeating units. The proportion (molar ratio) of the chlorinated-ether residue represented by the formula (1) to the chlorinated-ether residue represented by the formula (2) can be estimated from the proportion of secondary to primary terminal hydroxyl groups which can be calculated through NMR analysis. The range thereof is preferably from 1/99 to 99/1, more preferably from 20/80 to 80/20.

The chlorinated polyether of the invention may have hydroxyl groups at the polymer ends, branch chain ends, etc., like the generally known polyethers (sometimes referred to as polyether polyols). The amount of hydroxyl groups in the chlorinated polyether of the invention can be calculated in terms of hydroxyl value (mg-KOH/g). The hydroxyl value of the chlorinated polyether is not particularly limited, and can be set according to intended uses. For use as a starting material for polyurethanes, a chlorinated polyether having a hydroxyl value of 1-1,000 (mg-KOH/g) is preferred. Incidentally, hydroxyl value can be calculated in accordance with the method described in JIS K1557.

The molecular weight of the chlorinated polyether of the invention is not particularly limited, and this polyether may have any molecular weight. In the case where the chlorinated polyether of the invention is to be used as a starting material for polyurethanes, it is preferred that the chlorinated polyether should have a number-average molecular weight of 200-10,000 because this chlorinated polyether has excellent handleability and brings about excellent polyurethane production efficiency. Incidentally, the number-average molecular weight can be determined as a value calculated for standard polystyrene after an examination by gel permeation chromatography using tetrahydrofuran as a solvent.

For producing the chlorinated polyether of the invention, any desired method can be used so long as it is possible to produce a polymer containing, as a repeating unit, at least one of the chlorinated-ether residue represented by the above-described formula (1) and the chlorinated-ether residue represented by the above-described formula (2). Examples thereof include a process in which ring-opening polymerization of the chlorinated epoxy compound represented by the following formula (3) is conducted in the presence of an acid catalyst using an active-hydrogen-containing compound as a polymerization initiator.

[Chem. 4]

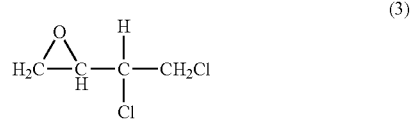

There are the cases where the chlorinated polyether obtained by the production process has hydroxyl groups like the generally known polyethers. The chlorinated-ether residue represented by the formula (1) and the chlorinated-ether residue represented by the formula (2) are attributable to a difference in reaction site which arose when the epoxy group of the chlorinated epoxy compound represented by the formula (3) underwent ring opening.

Examples of the polymerization initiator for use in this process generally include compounds containing active hydrogen, such as hydroxy compounds, amine compounds, carboxylic acid compounds, phenol compounds, phosphoric acid, and thiol compounds. More specific examples thereof include hydroxy compounds such as water, ethylene glycol, diethylene glycol, propylene glycol, 1,4-butanediol, 1,6-hexanediol, bisphenol A, glycerol, trimethylolpropane, hexanetriol, pentaerythritol, diglycerol, sorbitol, and sucrose; amine compounds such as ethylenediamine; carboxylic acid compounds such as benzoic acid and adipic acid; phenol compounds such as bisphenol A; and thiol compounds such as ethanedithiol and butanedithiol. These polymerization initiators may be used alone or as a mixture of several of these.

The amount of the polymerization initiator to be used is not particularly limited, and may be regulated by changing the proportion of the chlorinated epoxy compound represented by the formula (3) to the polymerization initiator according to the desired molecular weight of the chlorinated polyether. In particular, it is preferred to use the polymerization initiator in such an amount that the amount of the active hydrogen in the polymerization initiator is in the range of 0.02-2 mol per mol of the chlorinated epoxy compound represented by the formula (3), because a chlorinated polyether suitable for use as a starting material for polyurethanes is obtained.

As the acid catalyst, substances known as ordinary acid catalysts can be used. Examples thereof include mineral acids such as sulfuric acid, phosphoric acid, and hydrochloric acid; boron halide compounds such as boron trifluoride and boron trichloride; aluminum halide compounds such as aluminum chloride and aluminum bromide; tin compounds such as tin tetrafluoride and tin tetrachloride; antimony compounds such as antimony fluoride and antimony chloride; iron compounds such as ferric chloride; phosphorus compounds such as phosphorus pentafluoride; zinc halide compounds such as zinc chloride; titanium compounds such as titanium tetrachloride; zirconium compounds such as zirconium chloride; beryllium compounds such as beryllium chloride; organoboron compounds such as triphenylboron, tri(t-butyl)boron, tris(pentafluorophenyl)boron, bis(pentafluorophenyl)-t-butylboron, bis(pentafluoro-phenyl)boron fluoride, di(t-butyl)boron fluoride, and (pentafluorophenyl)boron difluoride; organoaluminum compounds such as triethylaluminum, triphenylaluminum, diphenyl-t-butylaluminum, tris(pentafluorophenyl) aluminum, bis(pentafluorophenyl)-t-butylaluminum, bis (pentafluorophenyl)aluminum fluoride, di(t-butyl)aluminum fluoride, (pentafluorophenyl)aluminum difluoride, and t-butylaluminum difluoride; and organozinc compounds such as diethyl zinc.

In the case where a Lewis acid is used as the acid catalyst, the acid may be used alone or may be used as a complex with any of various organic compounds. Examples of the complex of a Lewis acid with an organic compound include ether complexes such as dimethyl ether complexes, diethyl ether complexes, and THF (tetrahydrofuran) complexes; carboxylic acid complexes such as acetic acid complexes; alcohol complexes; amine complexes; and phenol complexes. Two or more acid catalysts may be used in combination.

The amount of the acid catalyst to be used is not particularly limited. In particular, it is preferred to use the acid catalyst in an amount in the range of $1\times10^{-5}$ to 0.1 mol per mol of the chlorinated epoxy compound represented by the formula (3), because such an acid catalyst amount enables a chlorinated polyether to be produced efficiently.

The chlorinated epoxy compound represented by the formula (3) is 3,4-dichloro-1,2-epoxybutane.

The chlorinated polyether of the invention may be produced either in a solvent or without using a solvent. In the case of producing a high-molecular-weight chlorinated polyether having high viscosity, use of a solvent is preferred. It is also possible to conduct the polymerization without using a solvent and thereafter add a solvent.

As the solvent, any solvent which does not influence the polymerization can be used without particular limitations. Examples thereof include hydrocarbons such as hexane and heptane; aromatic compounds such as toluene and xylene; chlorides such as methylene chloride, chloroform, dichloroethane, trichloroethane, and dichlorobenzene; ethers such as ethyl ether; nitro compounds such as nitromethane and nitrobenzene; sulfides such as carbon disulfide; and alkylene glycol dialkyl ethers such as propylene glycol dimethyl ether. These solvents may be used alone or as a mixture of two or more thereof.

The amount of the solvent to be used is not particularly limited. It is preferred that the weight of solvent should be up to 10 times the weight of the chlorinated epoxy compound represented by the formula (3) especially because such a solvent amount brings about an excellent efficiency of recovering the chlorinated polyether from the polymerization system.

With respect to production conditions, any conditions may be used so long as the ring-opening polymerization of the chlorinated epoxy compound represented by the formula (3) is possible. Examples thereof include polymerization temperatures in the range of −78 to 150° C. and polymerization times in the range of 10 minutes to 48 hours. It is preferred to use a polymerization temperature in the range of −50 to 120° C. and a polymerization time in the range of 30 minutes to 24 hours especially because a chlorinated polyether having excellent quality is obtained under such conditions.

The chlorinated polyether of the invention is useful as a starting material for polyurethanes, a starting material for polyesters, and a starting material for surfactants. In particular, the chlorinated polyether having hydroxyl groups is useful as a polyol for polyurethane foam, a polyol for urethane-based sealing materials, a polyol ingredient for urethane adhesives, a polyol ingredient for urethane elastomers, a binder ingredient, primer ingredient, or sealer ingredient for urethane coating materials, a varnish ingredient for inks, a flame retardant for polyurethanes, etc.

By subjecting the chlorinated polyether of the invention to reaction with any of various polyisocyanate compounds and optionally with a chain extender, a novel polyurethane can be obtained.

As the polyisocyanate compound, any compound having at least two isocyanate groups can be used. Examples thereof include 2,4-tolylene diisocyanate, 2,6-tolylene diisocyanate, 2,4'-diphenylmethane diisocyanate, 4,4'-diphenylmethane diisocyanate, polymethylene polyphenylene polyisocyanates, 1,5-naphthalene diisocyanate, tolidine diisocyanate, xylylene diisocyanate, 1,3-phenylene diisocyanate, 1,4-phenylene diisocyanate, lysine diisocyanate, triphenylmethane triisocyanate, tetramethylxylene diisocyanate, 1,6-hexamethylene diisocyanate, 4,4'-cyclohexylmethane diisocyanate, isophorone diisocyanate, 1,4-cyclohexane diisocyanate, norbornane diisocyanate, lysine ester triisocyanates, 1,6,11-undecane triisocyanate, 1,8-diisocyanato-4-isocyanatomethyloctane, 1,3,6-hexamethylene triisocyanate, bicycloheptane triisocyanate, trimethylhexamethylene diisocyanate, and mixtures of two or more of these. Examples thereof further include modifications (modifications containing a urethane group, carbodiimide group, allophanate group, urea group, biuret group, isocyanurate group, amide group, imide group, uretoneimine group, urethodione group, or oxazolidone group) of those polyisocyanates.

As the chain extender, any compound falling under the category of chain extenders for polyurethanes can be used. The chain extender preferably is a low-molecular compound having two or more active-hydrogen groups. Examples thereof include diols such as ethylene glycol, propylene glycol, 1,3-propanediol, 1,4-butanediol, 1,3-butanediol, 2,3-butanediol, 1,5-pentanediol, neopentyl glycol, 1,6-hexanediol, 3-methyl-1,5-pentanediol, 1,8-octanediol, 1,9-nonanediol, and hydroquinone diethylol ether; diamines such as ethylenediamine, propylenediamine, butylenediamine, hexamethylenediamine, cyclohexylenediamine, piperazine, tolylenediamine, 4,4'-diaminodiphenylmethane, 3,3'-dichloro-4,4'-diaminodiphenylmethane, xylylenediamine, hydrogenated 4,4'-diaminodiphenylmethane, hydrogenated xylylenediamine, isophoronediamine, and norbornanediamine; and mixtures of two or more of these.

Furthermore, a mixture of the chlorinated polyether of the invention and another polyol can be used as a starting material for urethanes. As this polyol, one in ordinary use for polyurethanes can be used. Examples thereof include polyether polyols obtained by the ring-opening polymerization of alkylene oxides, polymer polyols obtained by the radical polymerization of vinyl monomers in a polyether polyol; polyester polyols obtained by the co-condensation of a polyhydric alcohol with a polycarboxylic acid, polyester-amide polyols obtained by the co-condensation of a polyhydric alcohol with a polycarboxylic acid and an amino alcohol, polylactone polyols obtained by the ring-opening polymerization of lactones, polycarbonate polyols obtained by the co-condensation of a polyhydric alcohol with a carbonate, acrylic polyols, polybutadiene polyols and products of hydrogenation thereof, polyisoprene polyols and products of hydrogenation thereof, partly saponified ethylene/vinyl acetate copolymers, and polyols derived from natural oils such as soybean oil and castor oil.

EXAMPLES

The invention will be explained below by reference to Examples, but the Examples should not be construed as limiting the invention in any way.

<Analytical Instruments>

—Determination of Molecular Weight—

A gel permeation chromatograph (GPC) [(trade name) HLC 8020 GPC, manufactured by Tosoh Corp.] was used together with TSKgel GMHHR-L (trade name; manufactured by Tosoh Corp.) as a column and tetrahydrofuran as a solvent to obtain an elution curve at 40° C. Molecular weight was determined from the elution curve through a calculation for standard polystyrene.

—Examination for NMR Spectrum—

A nuclear magnetic resonance spectrophotometer [(trade name) GSX 270WB, manufactured by JEOL Ltd.] was used to make a measurement using deuteration chloroform as a deuteration solvent.

—Measurement of Thermal Decomposition Temperature (TG/DTA)—

An apparatus for both differential thermal analysis and thermogravimetry [(trade name) TG/DTA 6200, manufactured by SII Nano Technology Inc.] was used to conduct a measurement in air at a heating rate of 10° C./min.

Production Example

Production of 3,4-Dichloro-1,2-epoxybutane

Into a 5-liter four-necked flask equipped with a stirrer, condenser, thermometer, and nitrogen introduction tube were introduced 1,000 g (4.06 mol) of 70% m-chloroperbenzoic acid and 1,360 mL of chloroform. The resultant mixture was stirred to dissolve the m-chloroperbenzoic acid. Subsequently, 426 g (3.44 mol) of 3,4-dichloro-2-butene was added, and this mixture was subjected to reaction at 40° C. for 24 hours. Thereafter, the slurry solution was filtered, and the chloroform in the filtrate was removed with an evaporator to obtain a crude 3,4-dichloro-1,2-epoxybutane product. The crude 3,4-dichloro-1,2-epoxybutane product was distilled at a reduced pressure to obtain 335 g of purified 3,4-dichloro-1,2-epoxybutane.

Example 1

A 200-mL four-necked flask equipped with a stirrer, thermometer, and nitrogen introduction tube was heated and dried at a reduced pressure, and nitrogen displacement was conducted. Thereafter, 2.7 g (36 mmol) of propylene glycol as a polymerization initiator, 0.52 g of a boron trifluoride/ether complex as an acid catalyst, 30 g of methylene chloride as a polymerization solvent, and 30 g (214 mmol) of the 3,4-dichloro-1,2-epoxybutane obtained in Production Example were introduced thereinto, and polymerization reaction was conducted for 1 hour while stirring the mixture on an ice-water bath.

Subsequently, 25 mL of 1% aqueous sodium hydroxide solution was added, and the resultant mixture was stirred for 30 minutes. After the reaction mixture was subjected to oil-water separation, the organic layer was dried with anhydrous sodium sulfate. The anhydrous sodium sulfate and the methylene chloride were removed to thereby obtain 31 g of a viscous liquid. In $^1$H-NMR analysis, the protons of the methyl group of propylene glycol were observed at 1.2 ppm, and the protons of the methylene and methine of propylene glycol and the protons of the methylene and methine formed by the ring opening of the 3,4-dichloro-1,2-epoxybutane were observed at 3.4-4.4 ppm. It was hence ascertained that the viscous liquid was a chlorinated polyether obtained by the ring-opening polymerization of the 3,4-dichloro-1,2-epoxybutane.

$^{13}$C-NMR analysis revealed that the resultant chlorinated polyether was composed of the chlorinated-ether residue represented by the formula (1) and the chlorinated-ether residue represented by the formula (2) in a ratio of 50/50 (by mole). The chlorinated polyether had a hydroxyl value of 120, a number-average molecular weight of 800, and a 1% weight loss temperature in air of 174° C. The chlorinated polyether was soluble in methanol and acetone.

Example 2

A 200-mL four-necked flask equipped with a stirrer, thermometer, and nitrogen introduction tube was heated and dried at a reduced pressure, and nitrogen displacement was then conducted. Into the flask were introduced 3.2 g (36 mmol) of glycerol as a polymerization initiator, 0.52 g of a boron trifluoride/ether complex as an acid catalyst, and 15 g (107 mmol) of the 3,4-dichloro-1,2-epoxybutane obtained in Production Example. Polymerization reaction was conducted for 2 hours while stirring the mixture on an ice-water bath. Furthermore, 30 g of methylene chloride and 15 g (107 mmol) of the 3,4-dichloro-1,2-epoxybutane were added, and polymerization reaction was conducted for 1 hour with stirring.

Subsequently, 25 mL of 1% aqueous sodium hydroxide solution was added, and the resultant mixture was stirred for 30 minutes. After the reaction mixture was subjected to oil-water separation, the organic layer was dried with anhydrous sodium sulfate. The anhydrous sodium sulfate and the methylene chloride were removed to thereby obtain 32 g of a viscous liquid. In $^1$H-NMR analysis, the protons of the methylene and methine of glycerol and of the product of ring opening of the 3,4-dichloro-1,2-epoxybutane were observed at 3.6-4.4 ppm. It was hence ascertained that the viscous liquid was a chlorinated polyether obtained by the ring-opening polymerization of the 3,4-dichloro-1,2-epoxybutane.

$^{13}$C-NMR analysis revealed that the resultant chlorinated polyether was composed of the chlorinated-ether residue represented by the formula (1) and the chlorinated-ether residue represented by the formula (2) in a ratio of 50/50 (by mole). The chlorinated polyether had a hydroxyl value of 150, a number-average molecular weight of 400, and a 1% weight loss temperature in air of 189° C. The chlorinated polyether was soluble in methanol and acetone.

Example 3 to Example 12

In Example 3 to Example 8, polymerization was conducted by the method of Example 1 in which the amount of propylene glycol only was varied. Likewise, in Example 9 to Example 12, polymerization was conducted by the method of Example 2 in which the amount of glycerol only was varied. The results thereof are summarized in Table 1.

TABLE 1

| Example | Initiator | DCEB[1]/ initiator ratio (by mole) | Hydroxyl value (mg-KOH/g) | Mn[2] | Td[3] (° C.) |
|---|---|---|---|---|---|
| 3 | propylene glycol | 1.5 | 360 | 270 | 156 |
| 4 | propylene glycol | 2 | 300 | 400 | 160 |
| 5 | propylene glycol | 12 | 62 | 1400 | 179 |
| 6 | propylene glycol | 20 | 31 | 2000 | 185 |
| 7 | propylene glycol | 39 | 20 | 2900 | 152 |
| 8 | propylene glycol | 69 | 15 | 3200 | 188 |
| 9 | glycerol | 2 | 440 | 380 | 162 |
| 10 | glycerol | 12 | 91 | 1100 | 177 |
| 11 | glycerol | 29 | 37 | 1600 | 217 |
| 12 | glycerol | 59 | 23 | 1900 | 230 |

[1]DCEB: 3,4-dichloro-1,2-epoxybutane
[2]Number-average molecular weight calculated through GPC
[3]1% weight loss temperature in air The chlorinated polyethers obtained in Examples 3 to 12 each had a 1% weight loss temperature in air of 150° C. or higher, and were soluble in methanol and acetone.

Comparative Example 1

Into a 1,000-mL four-necked flask equipped with a stirrer, thermometer, condenser, and chlorine gas introduction tube were introduced 20 g of polypropylene glycol having a number-average molecular weight of 400 and 500 mL of carbon tetrachloride. Thereafter, the resultant mixture was heated to a temperature at which the carbon tetrachloride was gently refluxed, and chlorine gas was bubbled thereinto while irradiating the mixture with ultraviolet. Chlorination reaction was thus conducted. The liquid reaction mixture was suitably sampled, and the reaction was terminated at the time when the degree of chlorination reached 50%.

The carbon tetrachloride was removed at a reduced pressure to obtain 60 g of a chlorinated polypropylene glycol. This chlorinated polypropylene glycol had a 1% weight loss temperature in air, as determined by TG/DTA analysis, of 85° C., showing that it had poor thermal stability.

Comparative Example 2

Into a 1,000-mL four-necked flask equipped with a stirrer, thermometer, condenser, and chlorine gas introduction tube were introduced 20 g of polypropylenetriol having a number-average molecular weight of 400 and 500 mL of carbon tetrachloride. Thereafter, the resultant mixture was heated to a temperature at which the carbon tetrachloride was gently refluxed, and chlorine gas was bubbled thereinto while irradiating the mixture with ultraviolet. Chlorination reaction was thus conducted. The liquid reaction mixture was suitably sampled, and the reaction was terminated at the time when the degree of chlorination reached 50%.

The carbon tetrachloride was removed at a reduced pressure to obtain 61 g of a chlorinated polypropylenetriol. This chlorinated polypropylenetriol had a 1% weight loss temperature in air, as determined by TG/DTA analysis, of 98° C., showing that it had poor thermal stability.

Example 13

Into a 100 mL separable flask were introduced 20 g of the chlorinated polyether obtained in Example 1, 1 g of butanediol, and 2.8 mg of triethylenediamine. The resultant mixture was heated to 90° C. with stirring. Subsequently, 10.9 g of 4,4'-methylenediphenyl diisocyanate heated to 80° C. was added thereto, and this mixture was stirred. Thereafter, the system was evacuated to remove bubbles. The resultant mixture was poured into a petri dish in which a Teflon (registered trademark) sheet had been spread, and was then heated at 105° C. for 6 hours to allow urethane reaction to proceed. Thus, a polyurethane sheet was obtained.

Some of the resultant polyurethane sheet was cut out and dissolved in N,N-dimethylformamide, and this solution was examined by gel permeation chromatography. As a result, the sheet was found to be a polyurethane having a number-average molecular weight of 16,000.

Example 14

Into a 500-mL beaker made of polypropylene were introduced 20 g of the chlorinated polyether obtained in Example 2, 0.8 g of water, and 0.02 g of triethylenediamine. Furthermore, a solution prepared by mixing 0.3 mL of polydimethylsiloxane with 1 mL of methylene chloride was added thereto, and the resultant mixture was stirred. Subsequently, a solution prepared by mixing 0.1 mL of dibutyltin (II) dilaurate with 1 mL of methylene chloride was added thereto, and stirring was continued. Furthermore, 13 g of tolylene diisocyanate was added, and the resultant mixture was quickly stirred for 10 seconds. Fine foaming was observed in the mixture, and the foaming stopped after about 1 minute. Thus, polyurethane foam was obtained.

While the invention has been described in detail and with reference to specific embodiments thereof, it will be apparent to one skilled in the art that various changes and modifications can be made therein without departing from the spirit and scope thereof.

This application is based on a Japanese patent application filed on Jun. 10, 2008 (Application No. 2008-151472), the contents thereof being incorporated herein by reference.

INDUSTRIAL APPLICABILITY

According to the invention, it is possible to provide a chlorinated polyether which has excellent solubility in solvents and excellent thermal stability, gives a polyurethane having the excellent effect of improving the adhesion of coating materials, inks, and adhesives to polyolefins, can be expected to be usable as a flame retardant, and is useful also as a novel starting material for polyurethanes.

The invention claimed is:
1. A process for producing a chlorinated polyether, the process comprising conducting ring-opening polymerization of a chlorinated epoxy compound represented by the follow- ing formula (3) in the presence of an acid catalyst in the range of $1 \times 10^{-5}$ to 0.1 mol per mol of the chlorinated epoxy compound represented by the formula (3) using as a polymerization initiator an active hydrogen-containing compound which is at least one selected from the group consisting of ethylene glycol, propylene glycol, glycerol, pentaerythritol and sorbitol; wherein the amount of polymerization initiator provides 0.02 to 1.5 mol of active hydrogen per mol of the chlorinated epoxy compound represented by the formula (3), wherein the acid catalyst is selected from the group consisting of a boron halide compound and an organoboron compound, and the chlorinated polyether consists of:

repeating units of a chlorinated-ether residue represented by the following formula (1) and a chlorinated-ether residue represented by the following formula (2);

residue units derived from said polymerization initiator; and hydroxyl groups at the ends of the chlorinated polyether;

wherein a molar ratio of the chlorinated-ether residue represented by the following formula (1) to the chlorinated-ether residue represented by the following formula (2) is from 20/80 to 80/20,

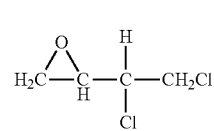
(3)

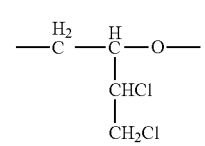
(1)

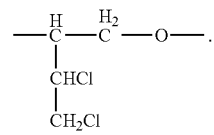
(2)

2. The process for producing the chlorinated polyether according to claim 1, wherein molar ratio of the chlorinated epoxy compound to the polymerization initiator is 1.5 to 69.

3. The process for producing the chlorinated polyether according to claim 1, wherein the polymerization initiator is propylene glycol or glycerol.

* * * * *